United States Patent [19]
Billy

[11] Patent Number: 5,295,356
[45] Date of Patent: Mar. 22, 1994

[54] PROCESS AND APPARATUS FOR THE PRODUCTION OF CARBON MONOXIDE AND HYDROGEN

[75] Inventor: Jean Billy, Le Plessie Trevise, France

[73] Assignee: L'Air Liquide, Societe Anonyme pour l'Etude et l'Exploitation des Procedes Georges Claude, Paris, France

[21] Appl. No.: 942,148

[22] Filed: Sep. 8, 1992

[30] Foreign Application Priority Data

Sep. 11, 1991 [FR] France ............... 91 11197

[51] Int. Cl.$^5$ .............................................. F25J 3/00
[52] U.S. Cl. ............................................ 62/20; 62/24; 62/40
[58] Field of Search ........................ 62/20, 23, 24, 40

[56] References Cited

U.S. PATENT DOCUMENTS

| | | | |
|---|---|---|---|
| 3,872,025 | 3/1975 | Singleton | 62/23 |
| 4,217,759 | 8/1980 | Shenoy | 62/23 |
| 4,888,035 | 12/1989 | Bauer | 62/20 |

FOREIGN PATENT DOCUMENTS

| | | |
|---|---|---|
| 0317851 | 5/1989 | European Pat. Off. . |
| 621453 | 7/1933 | Fed. Rep. of Germany . |
| 2353819 | 12/1987 | France . |

Primary Examiner—Ronald C. Capossela
Attorney, Agent, or Firm—Curtis, Morris & Safford

[57] ABSTRACT

The heating and/or the cooling of the three columns is ensured by a closed nitrogen cycle. Carbon monoxide is withdrawn in liquid form from the third column, then is brought through a pump at the pressure of utilization and is warmed under this pressure.

4 Claims, 1 Drawing Sheet

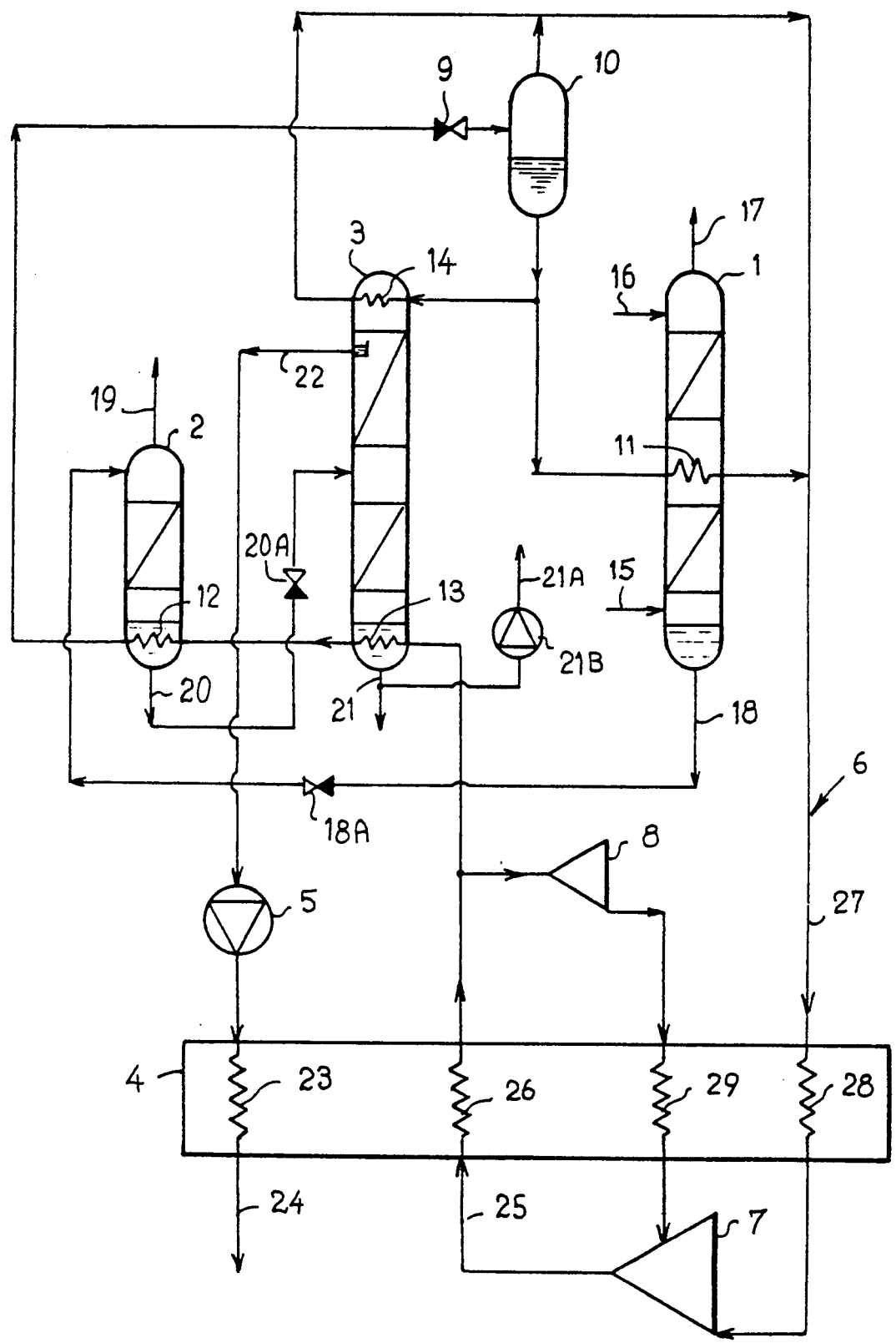

PROCESS AND APPARATUS FOR THE PRODUCTION OF CARBON MONOXIDE AND HYDROGEN

BACKGROUND OF INVENTION (a) Field of the Invention

The present invention relates to a process for the production of carbon monoxide and hydrogen from a gaseous mixture essentially comprising these two substances and methane, of the type in which: the starting gaseous mixture is washed with liquid methane in a first column to provide gaseous hydrogen and a washing liquid; the hydrogen which is dissolved in the washing liquid is separated from the latter in a second column, and the remaining liquid is separated by distillation in a third column to provide a carbon monoxide of production at the top of this third column.

(b) Description of Prior Art

In the known technique, in order to use only one single compressor for the entire apparatus, carbon monoxide is withdrawn in gaseous form from the third column and is used as a cycle gas to provide heating and/or cooling for the three columns.

This utilization of an open cycle of carbon monoxide has the following disadvantages:

on the one hand, the compression of carbon monoxide presents certain difficulties of achievement because for example of the possibility, during the compression, of giving chemical reactions producing a decomposition of the molecule of carbon monoxide leading to the formation of compounds (carbon, carbon dioxide, ... ) which reduce the reliability of the separation and compression unit;

on the other hand, the utilization of a cycle of carbon monoxide produces in the unit a mass of this gas which is present therein, in liquid and gaseous form, which is a source of a risk in case accident.

The invention, while relying on a single compressor for the whole apparatus, aims at overcoming these disadvantages, i.e. eliminating the risks associated with the compression of gaseous carbon monoxide and reducing the potential risks associated with the mass of gaseous and liquid carbon monoxide which is present in the apparatus.

SUMMARY OF INVENTION

For this purpose, it is an object of the invention to provide a process of the type mentioned above, characterized in that each column is heated and/or cooled by means of a closed refrigerating cycle, and in that the carbon monoxide produced is withdrawn from the third column in liquid form, then is brought by means of a pump to the pressure of utilization and is heated under this utilization pressure.

The refrigerating cycle may for example be a nitrogen cycle.

It is also an object of the invention to provide an apparatus enabling to use such a process. This apparatus, of the type comprising: a first column provided at the bottom with an inlet of said gaseous mixture and at the top with an inlet of liquid methane; a second column provided at the bottom with a vaporizer and at the top with an inlet of liquid connected to the bottom of the first column; a third column provided at the bottom with a vaporizer, at the top with means for providing a reflux and means for withdrawing carbon monoxide, and at an intermediate point, an inlet connected to the bottom of the second column; and a refrigerating cycle ensuring the heating and/or the cooling of the three columns, is characterized in that the refrigerating cycle is a closed cycle, and in that the means for withdrawing carbon monoxide are means for withdrawing liquid connected to the suction side of a pump, the apparatus comprising means for warming fluid delivered by this pump.

DESCRIPTION OF DRAWINGS

An example of an embodiment of the invention will now be described with reference to the annexed drawings, in which the single FIGURE is a schematic representation of an apparatus for the production of carbon monoxide and hydrogen according to the invention.

DESCRIPTION OF PREFERRED EMBODIMENTS

The apparatus illustrated in the drawings is intended to produce gaseous carbon monoxide (CO) under pressure and gaseous hydrogen also under pressure, from a initial gaseous mixture essentially containing carbon monoxide, hydrogen and methane. This mixture, which is for example a reforming gas or a gas resulting from the partial oxidation of hydrocarbons, previously dried and decarbonized, generally contains small quantities of heavy impurities $C_xH_y$ and impurities which are lighter than CO such as nitrogen and argon.

The apparatus essentially comprises a first column, or washing column, 1, a second column 2, a third column, or distillation column, 3, a heat exchanger 4 of the indirect and circulation type in counter-current to fluids in heat exchange relationship, pump 5, and a refrigerating cycle 6. This cycle 6 comprises a compressor 7, an expansion turbine 8, an expansion valve (9) and a phase separator 10.

To ensure the heating and/or cooling of the three columns 1 to 3 by means of the refrigerating cycle 6, column 1 includes at an intermediate level a condenser 11, column 2 includes at the bottom a vaporizer 12 and column 3 includes at the bottom a vaporizer 13 and at the top a condenser 14.

The initial gaseous mixture, introduced at the bottom of column 1, via duct 15, under a pressure for example of the order of 15 to 40 bars absolute, is washed in this column by means of liquid methane introduced at the top of the column via duct 16, an intermediate refrigeration of the column being ensured by condenser 11.

A gaseous production flow of hydrogen, under pressure, is withdrawn at the top of column 1 via duct 17, while the bottom liquid, essentially consisting of carbon monoxide, methane and hydrogen, is sent, via duct 18 provided with an expansion valve 18A, to the top of column 2. The latter being heated at the bottom by means of vaporizer 12, the hydrogen dissolved is separated from the liquid in this second column, under a pressure of the order of 5 to 10 bars, and is withdrawn at the top via a duct 19.

The liquid at the bottom of column 2, essentially consisting of methane and carbon monoxide, is introduced, via duct 20, provided with an expansion valve 20A, at an intermediate point of column 3. The latter, heated at the bottom by means of vaporizer 13 and cooled at the top with condenser 14, separates the two components of the liquid by distillation under a pressure of the order to 1 to 2.5 bars. Liquid methane containing heavy impurities is withdrawn at the bottom of column 3 via duct 21, and liquid carbon monoxide containing light impurities is withdrawn at the top of the same column via duct 22.

While the liquid methane is partly blown off and partly recycled, via duct 21A provided with a pump 21B, into duct 16 which feeds the top of column 1, the liquid carbon monoxide is brought to the desired pressure of utilization by means of pump 5, then it is warmed under this pressure in ducts 23 of the heat exchanger 4, from where it exists in the form of gaseous product via duct 24.

The refrigerating cycle 6 which is a closed nitrogen cycle, i.e. whose fluid cycle is nitrogen and which is entirely separated from the above mentioned fluid cycles, will now be described.

The cycle nitrogen, compressed by compressor 7 in high pressure duct 25, is cooled in ducts 26 of the exchanger 4, then condensed in vaporizers 13 and 12. The high pressure liquid nitrogen is expanded in expansion valve 9 and separated into two phases in separator 10. The low pressure gaseous nitrogen which is produced by this separator is sent via duct 27 and ducts 28 of the exchanger 4 to the low pressure suction side of the compressor, while low pressure liquid nitrogen is vaporized in condensers 11 and 14, the gaseous nitrogen resulting from these vaporizations also being sent to duct 27. A fraction of the high pressure gaseous nitrogen which exits from ducts 26 is expanded in turbine 8 at an intermediate pressure and is warmed in ducts 29 of the exchanger 4 and sent back to an intermediate stage of the compressor 7.

The apparatus described above enables to reduce to a minimum the mass of carbon monoxide which is present therein, such as due to the fact that the mass of fluid of the cycle stored in liquid form in separator 10, generally used as cold reserve, consists of nitrogen.

We claim:

1. Process for the production of carbon monoxide and hydrogen from a gaseous mixture comprising these two substances and methane comprising the steps of:

washing an initial gaseous mixture of carbon monoxide and hydrogen with liquid methane in a first column to obtain gaseous hydrogen and a washing liquid;

separating hydrogen dissolved in the washing liquid in a second column to obtain a remaining liquid comprising carbon monoxide and methane;

separating the remaining liquid by distillation in a third column to withdraw carbon monoxide in liquid form for production at a top section of said third column;

pressurizing the liquid carbon monoxide to a predetermined pressure of utilization by pumping means;

heating the liquid carbon monoxide under said utilization pressure; and heating and/or cooling each of said columns by means of a closed refrigerating cycle.

2. The process according to claim 1, wherein the closed refrigerating cycle is a nitrogen cycle.

3. Apparatus for the production of carbon monoxide and hydrogen from a gaseous mixture comprising these two substances and methane comprising:

a first column having at its bottom a first inlet for receiving the gaseous mixture comprising carbon monoxide and hydrogen and at its top a second inlet for receiving liquid methane;

a second column receiving at its top a liquid comprised of carbon monoxide, methane and hydrogen from said first column and having at its bottom a vaporizer to separate hydrogen from the carbon monoxide and methane;

a third column having at an intermediate point thereof an inlet for receiving a liquid mixture comprising carbon monoxide and methane from the bottom of said second column and having at its bottom a vaporizer for heating the liquid mixture and at its top means for providing reflux and means for withdrawing liquid carbon monoxide including pumping means for pressurizing the liquid carbon monoxide to a desired pressure of utilization;

means for heating the liquid carbon monoxide delivered by said pumping means to provide a gaseous product; and a refrigeration cycle providing for heating and/or cooling of said columns with said refrigeration cycle operating in a closed cycle.

4. The apparatus according to claim 3 wherein the refrigeration cycle is a nitrogen cycle.

* * * * *